United States Patent [19]

Fassbind

[11] Patent Number: 4,902,275

[45] Date of Patent: Feb. 20, 1990

[54] COTTON APPLICATOR

[75] Inventor: Karl Fassbind, Mannedorf, Switzerland

[73] Assignee: Fassbind & Fassbind, Mannedorf, Switzerland

[21] Appl. No.: 96,267

[22] Filed: Sep. 8, 1987

Related U.S. Application Data

[63] Continuation of Ser. No. 635,189, Jul. 27, 1984, abandoned, which is a continuation-in-part of Ser. No. 581,195, Feb. 17, 1983, abandoned.

[30] Foreign Application Priority Data

Mar. 1, 1983 [SE] Sweden .................................. 1123/83

[51] Int. Cl.⁴ .............................................. A61M 35/00
[52] U.S. Cl. ......................................... 604/1; 606/131
[58] Field of Search ........................................ 604/1-3, 604/55, 309, 328, 385.1, 904; 128/304, 342; D24/59, 67, 99

[56] References Cited

U.S. PATENT DOCUMENTS

| D. 198,115 | 4/1964 | Wittke et al. | D24/63 |
| D. 229,516 | 12/1973 | Scheurer et al. | D24/63 |
| D. 264,249 | 5/1982 | Leight | D24/67 |
| 1,388,960 | 8/1921 | Lerch . | |
| 1,693,581 | 11/1928 | Etling | 128/304 |
| 1,980,826 | 11/1934 | Reiss | 128/304 |
| 2,006,539 | 7/1935 | Deford | 604/1 |
| 2,510,961 | 6/1950 | Davis | 604/1 |
| 2,948,280 | 8/1960 | Vicik | 128/304 |
| 2,987,063 | 6/1961 | Glickston | 604/1 |

FOREIGN PATENT DOCUMENTS

| 0604145 | 10/1934 | Fed. Rep. of Germany . | |
| 2277557 | 2/1976 | France . | |
| 0447352 | 5/1936 | United Kingdom | D24/67 |

Primary Examiner—C. Fred Rosenbaum
Assistant Examiner—Sharon Rose
Attorney, Agent, or Firm—Anthony A. O'Brien

[57] ABSTRACT

A cotton applicator is disclosed as including a support rod and a cotton pledget disposed on an end thereof with the pledget having forward and rearward sections; the rearward section is about twice the diameter of the forward section with an annular shoulder therebetween whereby the forward section is limited in its penetration into an ear canal by the annular shoulder and the rearward section. The support rod axially extends through the rearward section and partially into the forward section whereby adequate support is provided for each section.

1 Claim, 1 Drawing Sheet

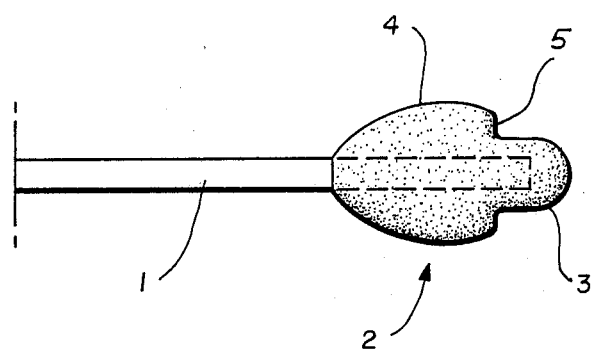

COTTON APPLICATOR

CROSS-REFERENCE TO RELATED APPLICATION

This application is a continuation of application Ser. No. 06/635,189 filed July 27, 1984 (abandoned), which application is a continuation-in-part application of application Ser. No. 581,195 filed Feb. 17, 1983, now abandoned.

BACKGROUND OF THE INVENTION

1. Technical Field of The Invention

The present invention relates to an improved cotton applicator including a supporting rod having a pledget of cotton on at least one of its ends.

Such cotton applicators are widely utilized for cleaning purposes. They are used for instance for hygienical purposes relating to ears and nose and the probably largest field of use is the cleaning of the auditory canal.

2. Description of The Prior Art

Generally known cotton applicators lead to problems and difficulties particularly with respect to a cleaning of the auditory canal that may be dangerous due to the pledget of cotton penetrating too deep into the auditory canal possibly giving rise to considerable injuries or defects. It is not only possible that the drumskin of the ear may suffer an injury but an excessive penetration of the pledget of cotton into the auditory canal may displace a cerumen clot deep into the auditory canal; such a cerumen clot pushed deeply within the auditory canal must be flushed out by a physician by means of water flushing procedures operating at rather high water pressures. It is, furthermore, known that an extremely deep penetration of the pledget of cotton within the auditory canal has often led to injuries of the inner auditory canal as well as of the drumskin of the ear.

The prior art is exemplified by U.S. Pat. No. 2,987,063 issued June 6, 1961 to S. W. Glickston, which discloses a swab applicator made of a longitudinal stick with a swab of absorbent cotton disposed on each end of the stick.

The above mentioned Glickston patent discloses a swab applicator which includes a necked-down portion between its body portion and a spherical end portion. This arrangement has many defects when used for ear treatment, e.g., the spherical end only provides a circumferential treating area of the ear canal whereas a cylindrical area would treat most of the cylindrical wall of the ear canal; the body portion is only slightly larger in diameter than the spherical end and the increasing annular taper would enhance entry into the ear rather than limiting penetration of the spherical end in the ear canal; the neck portion forms a weak spot whereby the spherical end could be separated from the applicator; the support rod is only in the body portion and thus cannot lend any support to the neck portion or spherical end whereby separation could result as when the spherical end could be prevented from rotating by ear wax stuck to the forward part of the spherical end.

OBJECTS OF THE INVENTION

It is an object of the present invention to construct economically and simply an improved cotton applicator with a pledget of cotton obviating injuries to the ear or the like when used therein.

Another object of this invention is to avoid detrimental situations in cleaning the ear or the like by preventing an excessively deep penetration of a pledget of cotton thereinto.

This invention has a further object in that the penetrating end of a cotton applicator is constructed to treat the major portion of the cylindrical wall area of a cavity.

A further object of this invention is to prevent separation of the penetrating end from the main body of a cotton applicator during rotation in a cavity.

SUMMARY OF THE INVENTION

A cotton applicator for treating an ear cavity or the like includes a longitudinal rod having at least one supporting end; a pledget of cotton on the supporting end including a cylindrical forward section adapted to fit into the cavity, a rearward section larger in diameter than the forward section and adapted to abut a perimeter of the cavity and limit penetration of the forward section into the cavity, and the supporting end of the rod extending axially through the rearward section and partially into the forward section to maintain support therefor during rotary use of the applicator.

BRIEF DESCRIPTION OF THE DRAWING

The present invention will be more fully understood by reference to the following detailed description thereof when read in conjunction with the attached drawing in which the single figure illustrates on an enlarged scale an elevational view of a cotton applicator embodying the present invention.

DETAILED DESCRIPTION

As is illustrated in the drawing, the present invention is embodied in a cotton applicator which includes a supporting rod 1 having a pledget 2 of cotton on at least one end of such rod. The cotton pledget 2 is formed with a generally cylindrical free end or forward section 3, a body or rearward section 4 having a generally bulbous configuration, and an annular wall or shoulder 5 extending transversely between the cylindrical section 3 and the bulbous section 4.

The end of the bulbous section 4 is mounted on the end of the supporting rod 1. As is shown in the drawing, the rod defines a longitudinal axis on which the cotton pledget 2 is disposed. The supporting end of the rod 1 axially extends completely through the rearward bulbous section 4 but only partially enters the forward cylindrical section 3. As is illustrated in the drawing the supporting end of rod 1 terminates at the approximate mid-point of the longitudinal dimension of the forward cylindrical section 3. With the end of rod 1 terminating in the forward cylindrical section 3, there is adequate support for section 3 to prevent its tearing and separation from the bulbous section 4. With this arrangement, there is sufficient support to prevent bending of the forward cylindrical section 3, which anti-bending feature is enhanced by the annular shoulder 5 which increases in diameter from the cylindrical section 3 of the bulbous section 4.

The bulbous section 4 has a major diameter which is approximately twice as large as the diameter of the cylindrical section 3. Like any bulb-shaped object, the rearward portion of the bulbous section 4 decreasingly tapers variably, and its rearmost part meets the support rod 1. The forward portion of the bulbous section 4 is defined by the annular shoulder or wall 5 which abuts the entry perimeter of the cavity and functions as a safety portion to limit the penetration of the cylindrical section 3 into the cavity of an ear or the like. The annular wall 5 has inner and outer diameters that are approximately the same as the contiguous parts of the cylindrical section 3 and the bulbous section 4, respectively. The cylindrical section 3 conforms in shape and size to the generally cylindrical wall of the cavity so that the cylindrical section 3 is able to treat a large surface area of the cavity wall.

The cotton forming the pledget is not deformed or compressed but rather remains in its original soft condition throughout each of its sections 3 and 4. Due to the large amount of cotton in the bulbous section 4, it cannot enter the auditory canal so that the cylindrical section 3 will not dislocate a cerumen clot. Insertion of the cotton applicator into an auditory canal provides penetration of the cylindrical section 3 until the limit of penetration is reached. Such an arrangement prevents injuries even when the applicator is handled by children.

Inasmuch as the present invention is subject to many variations, modifications and changes in details, it is intended that all matter contained in the foregoing description or shown in the accompanying drawing shall be interpreted as illustrative and not in a limiting sense.

I claim:

1. A cotton applicator for use in a cavity defined by an ear and the like comprising a unitary rod being disposed on a longitudinal axis so as to be linear along its entire length, a pledget of cotton on said supporting end adapted for unitary rotation therewith, said pledget of cotton including a forward generally cylindrical section of uniform diameter throughout its length, a generally bulbous rearward section having a major diameter approximately twice as large as the diameter of the cylindrical section and an annular wall extending transversely between the cylindrical and bulbous sections said supporting end of said rod extending axially through the bulbous section and terminating at the approximate mid-point of the cylindrical section to enhance support for the cylindrical section during rotary use of the applicator about said longitudinal axis and thereby avoid separation of the cynlindrical section from the bulbous section, said bulbous section tapering decreasingly from the major diameter of said annular wall to the diameter of said cylindrical section rearwardly thereof, said annular wall having inner and outer diameters the same as the diameter of said cylindrical section and the major diameter of said bulbous section, respectively, said annular wall engagable with an outside perimeter of the cavity and thereby limit penetration of the cylindrical section into the cavity.

* * * * *

UNITED STATES PATENT OFFICE
CERTIFICATE OF CORRECTION

Patent No. 4,902,275          Dated 2/20/90

Inventor(s)   FASSBIND, Karl

It is certified that error appears in the above-identified patent and that said Letters Patent is hereby corrected as shown below:

On the front page line "[30]" change "[SE] Sweden" to -- [SW] Switzerland -- .

Signed and Sealed this

Twenty-sixth Day of February, 1991

Attest:

HARRY F. MANBECK, JR.

*Attesting Officer*          *Commissioner of Patents and Trademarks*

UNITED STATES PATENT AND TRADEMARK OFFICE
CERTIFICATE OF CORRECTION

PATENT NO.   : 4,902,275
DATED        : 2/20/90
INVENTOR(S)  : Karl Fassbind

It is certified that error appears in the above-identified patent and that said Letters Patent is hereby corrected as shown below:

In claim 1 at Column 4, between lines 2 and 3 insert the following clause:

--     said rod having at least one supporting end on said longitudinal axis, --.

In claim 1 at column 4 after "sections" at the end of line 11, insert a comma -- , --.

Signed and Sealed this

Seventeenth Day of November, 1992

*Attest:*

DOUGLAS B. COMER

*Attesting Officer*     *Acting Commissioner of Patents and Trademarks*